(12) United States Patent
Narizuka et al.

(10) Patent No.: US 6,376,712 B2
(45) Date of Patent: Apr. 23, 2002

(54) PROCESS FOR PRODUCING TRIFLUOROMETHYLBENZYLAMINES

(75) Inventors: Satoru Narizuka; Eri Tsukada; Takashi Kume, all of Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/833,211

(22) Filed: Apr. 12, 2001

(30) Foreign Application Priority Data

Apr. 13, 2000 (JP) ............................ 12-112629

(51) Int. Cl.$^7$ ..................... C07C 211/00; C07C 204/00

(52) U.S. Cl. ....................................... 564/385; 504/384

(58) Field of Search ................................. 504/384, 385

(56) References Cited

PUBLICATIONS

Freifelder et al., "Preparation of Isomeric Trifluoromethyl-benzylamines", J. Pharm. Sci., 54 (1965), p. 1204.

Meindl et al., "Benzylamines: Synthesis and Evaluation of Antimycobacterial Properties", J. Med. Chem. 1984, 27, pp. 1111–1118.

*Primary Examiner*—Samuel Barts
(74) *Attorney, Agent, or Firm*—Crowell & Moring LLP

(57) ABSTRACT

The present invention relates to a process for producing a trifluoromethylbenzylamine represented by the general formula (1),

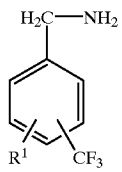

(1)

where $R^1$ represents hydrogen atom, a halogen atom selected from the group consisting of fluorine, chlorine, bromine and iodine, or trifluoromethyl group. This process includes the step of reducing an oxime by hydrogen in an organic solvent in the presence of a catalyst and ammonia. The oxime is represented by the general formula (2),

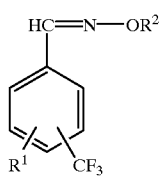

(2)

where $R^1$ is defined as above, and $R^2$ represents hydrogen atom, an alkyl group or an aralkyl group. With this process, the trifluoromethylbenzylamine can be produced with high yield.

11 Claims, No Drawings

PROCESS FOR PRODUCING TRIFLUOROMETHYLBENZYLAMINES

CROSS-REFERENCE TO RELATED APPLICATIONS

This application is related to copending application Ser. No. 09/532,004, entitled "PROCESS FOR PRODUCING TRIFLUOROMETHYLBENZYLAMINES", filed on Mar. 21, 2000.

BACKGROUND OF THE INVENTION

The present invention relates to a process for producing trifluoromethylbenzylamines.

Trifluoromethylbenzylamines represented by the general formula (1) are important compounds, for example, as intermediates for producing medicines and agricultural chemicals.

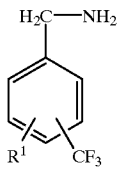
(1)

J. Pharm Sci., 54, 1204 (1965) discloses a process for producing a trifluoromethylbenzylamine by a catalytic reduction of trifluoromethylbenzonitrile in the presence of a catalyst. J Med. Chem., 27, 1111 (1984) discloses a process for producing a trifluoromethylbenzylamine by reducing a trifluoromethylbenzaldehyde oxime using a lithium aluminum hydride.

In the above mentioned conventional processes, since the former process uses a large amount of catalyst while not being satisfactory in terms of yield, and the latter process involves the use of hazardous substances requiring non-aqueous conditions while also not achieving a high yield, both of these processes have not been able to achieve satisfactory results as production processes applied on an industrial scale.

SUMMARY OF THE INVENTION

It is therefore an object of the present invention to provide a process for producing a trifluoromethylbenzylamine with high yield.

According to the present invention, there is provided a process for producing a trifluoromethylbenzylamine represented by the general formula (1),

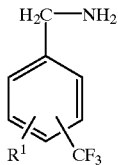
(1)

where $R^1$ represents hydrogen atom, a halogen atom selected from the group consisting of fluorine, chlorine, bromine and iodine, or trifluoromethyl group. This process comprises reducing an oxime by hydrogen in an organic solvent in the presence of a catalyst and ammonia. This oxygen is represented by the general formula (2),

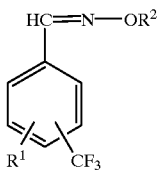
(2)

where $R^1$ is defined as above, and $R^2$ represents hydrogen atom, an alkyl group or an aralkyl group. This oxime can be obtained by reacting a trifluoromethylbenzaldehyde represented by the general formula (3) with a hydroxylamine represented by the general formula (4),

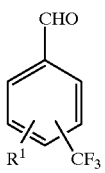
(3)

where $R^1$ is defined as above,

$$H_2NOR^2 \quad (4)$$

where $R^2$ is defined as above,

According to the process of the present invention, it becomes possible to produce the trifluoromethylbenzylamine at high yield and high selectivity, while also allowing each reaction step to be carried out under mild conditions. Therefore, this process is very effective in producing the target product in an industrial scale.

DESCRIPTION OF THE PREFERRED EMBODIMENTS

The oxime represented by the general formula (2) can be produced by the first step of reacting a trifluoromethylbenzaldehyde represented by the general formula (3) with a hydroxylamine represented by the general formula (4). As stated above, the trifluoromethylbenzaldehyde is represented by the general formula (3) in which $R^1$ is hydrogen atom, a halogen atom selected from fluorine, chlorine, bromine and iodine, or trifluoromethyl group. Examples of the trifluoromethylbenzaldehyde, represented by the general formula (3), include 2-trifluoromethylbenzaldehyde, 3-trifluoromethylbenzaldehyde, 4-trifluoromethylbenzaldehyde, 3-fluoro-4-trifluoromethylbenzaldehyde, 2-fluoro-5-trifluoromethylbenzaldehyde, 2-chloro-3-trifluoromethylbenzaldehyde, 2-chloro-5-trifluoromethylbenzaldehyde, 4-chloro-3-trifluoromethylbenzaldehyde, 3,5-bis(trifluoromethyl) benzaldehyde, 2,4-bis(trifluoromethyl)benzaldehyde, 2,6-bis(trifluoromethyl)benzaldehyde and 2,5-bis (trifluoromethyl)benzaldehyde.

As stated above, the hydroxylamine is represented by the general formula (4) in which $R^2$ is hydrogen atom, an alkyl group or an aralkyl group. Specific examples of the hydroxylamine are alkylhydroxylamines having 1 to 10 carbon atoms, such as hydroxylamine, O-methylhydroxylamine, O-ethylhydroxylamine, O-propylhydroxylamine, O-isopropylhydroxylamine, O-n-butylhydroxylamines, O-isobutylhydroxylamine, O-amylhydroxylamine, O-hexylhydroxylamine, O-heptylhydroxylamine, O-octylhydroxylamine, O-2:ethylhexylhydroxylamine, O-nonylhydroxylamine and O-decylhydroxylamine. Further specific examples of the hydroxylamine are aralkylhydroxylamines such as O-benzylhydroxylamine, O-p-tolylmethylhydroxylamine and O-phenethylhydroxylamine.

In the first step of the process, the hydroxylamine may be an acid salt of hydroxylamine, and this acid salt is formed by a reaction of the hydroxylamine with an acid such as hydrochloric acid, sulfuric acid, or a carboxylic acid. In the case of using an acid salt of the hydroxylamine, a hydroxylamine obtained by neutralizing in advance the acid salt with a base may be used in the first step. Alternatively, an acid salt of the hydroxylamine may be reacted with a trifluoromethylbenzaldehyde represented by the general formula (3) in the presence of a base, resulting in generation of a hydroxylamine, while simultaneously allowing a reaction of this hydroxylamine with the trifluoromethylbenzaldehyde, thereby obtaining an oxime represented by the general formula (2). The base used in the process is preferably the one inert in the hydrogenation. Preferable examples of the base that can be used include organic bases such as pyridine, triethylamine and N-methylmorpholine, and inorganic bases such as sodium bicarbonate, sodium carbonate, potassium bicarbonate, potassium carbonate, calcium carbonate, lithium hydroxide, sodium hydroxide and potassium hydroxide. The amount of the base used in the process is preferably at least 1 mole, and more preferably 1 to 10 moles, per mol of an acid salt of the hycdroxylamine.

In the first step of the process, any solvent that is inert in the reaction can be used. Examples of solvents that can be used in the first step include ether-based, alcohol-based, amide-based, nitrile-based, aliphatic hydrocarbon-based, aromatic hydrocarbon-based, amine-based and halogenated hydrocarbon-based solvents. Typical examples of these solvents include tetrahydrofuran, diethyl ether, methanol, ethanol, dimethylformamide, acetonitrile, hexane, benzene, toluene, pyridine, triethylamine, chloroform, methylene chloride and chlorobenzene, and two or more of these solvents can be used in combination.

The reaction temperature is normally −20 to 150° C., and although there are no particular restrictions on this temperature, the reaction proceeds smoothly even in the vicinity of room temperature.

The oxime represented by the general formula (2) is obtained nearly quantitatively from the reaction mixture obtained in the reaction of the first step by procedures such as extraction, liquid separation, concentration, distillation and crystallization. In some cases, the oxime may be able to be used in the next step (second step) while still in the form of the reaction mixture without being isolated. Furthermore, although there are two types of isomers present in the oxime obtained by the first step, that is, the syn form and anti form, the oxime can be used either in the form of a single isomer or as a mixture of both isomers in the second step of the present invention.

Next, the following provides an explanation of the second step of the process in which the trifluoromethylbenzylamine represented by the general formula (1), the final target product, is obtained by reduction of the oxime represented by the general formula (2).

In the second step, the reaction product (oxime) obtained by the first step can be reduced by catalytic hydrogenation. Although both heterogeneous and homogeneous catalysts can be used as the catalyst of the catalytic hydrogenation, heterogeneous catalysts are preferable in consideration of their ease of removal. Thus, metals or metal oxides such as palladium or platinum oxide, or these supported on a carrier such as activated carbon, alumina or diatomaceous earth, can be used. Examples of the catalyst include palladium-loaded activated carbon, palladium hydroxide-loaded activated carbon, palladium-loaded barium sulfate, palladium-loaded calcium carbonate, palladium-loaded strontium carbonate, palladium black, palladium-loaded silica gel, platinum dioxide, platinum-loaded activated carbon, platinum black, Raney nickel, ruthenium-loaded activated carbon and rhodium-loaded activated carbon. Although the amount of the catalyst may vary according to its type, it is preferably 0,0001–1 mol %, more preferably 0.001–0.1 mol %, based on the number of moles of the oxime.

Examples of the reaction solvent used in the second step include alcohols, hydrocarbons, ethers, carboxylic acids, esters, and amides. Typical examples of these solvents include methanol, ethanol, benzene, toluene, xylene, ethyl benzene, isopropyl benzene, tetralin, mesitylene, tetrahydrofuran, diethyl ether, acetic acid, ethyl acetate and dimethylformamide, and two or more types of these solvents can be used in combination.

Hydrogen pressure for conducting catalytic hydrogenation of the second step may vary according to the solvent type, the catalyst type and other conditions. Although a pressure within the range of normal pressure (atmospheric pressure) to about 100 atmospheres can be used, a pressure of 5 atmospheres or more is used preferably.

In the second step, although a temperature within the range of −10° C. to the boiling point of the solvent can be normally used for the reaction temperature, a temperature of roughly 0–50° C. is preferable, and the object of the second step can be sufficiently achieved even at room temperature (10–30° C.).

In the second step, ammonia is added to the reaction system to improve the selectivity of the reaction to obtain the trifluoromethylbenzylamine represented by the general formula (1). This ammonia can be added to the reaction system in the form of liquid ammonia or by dissolving in the reaction solvent. The amount of this ammonia is not particularly limited, and it is preferably 1–10 moles, more preferably 3–5 moles, to 1 mole of the oxime represented by the general formula (2).

After separating the catalyst from the reaction mixture obtain ed by the reaction of the second step, the trifluoromethylbenzylamine represented by the general formula (1) can be obtained at an extremely high yield by a procedure such as concentration.

As shown in the general formula (1), the target compound, trifluoromethylbenzylamine, has an amino group at the benzyl position. It is generally known that an amino group at the benzyl position tends to be eliminated by the occurrence of hydrogenolysis by catalytic hydrogenation. Therefore, there was also concern over elimination of the amino group in the target compound of the present invention as well. However, according to the present invention, the elimination reaction of the amino group unexpectedly hardly occurs at all, and the target compound can be obtained both selectively and at significantly high yield.

The hydrogenation reaction of the oxime compound of the second step is believed to go through a reaction intermediate (5) as shown in the following reaction scheme.

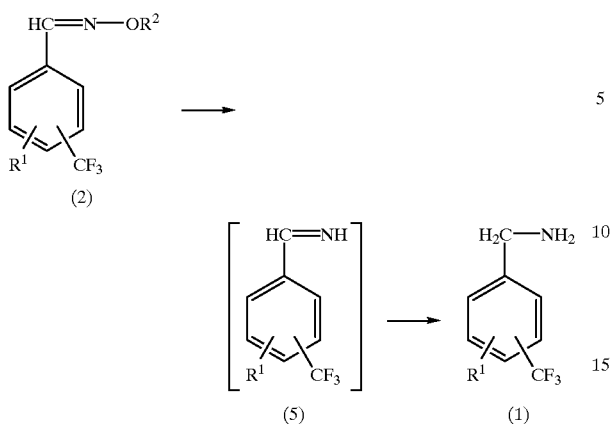

Similar to the oxime represented by the general formula (2), since this reaction intermediate (5) has one or two trifluoromethyl groups, which are extremely powerful electron attracting groups, on the benzene ring, the reaction intermediate (5) is susceptible to attack by various nucleophiles such as water and the target compound of the present invention. There was therefore concern over decreased selectivity for the target compound due to the formation of benzyl alcohol and secondary amine as by-products. However, according to the process of the present invention, there is unexpectedly hardly any formation of reaction by-products such as addition products, and the target compound represented by the general formula (1) can be obtained both selectively and at remarkably high yield.

Examples of the trifluoromethylbenzylamine represented by the general formula (1) include 2-trifluoromethylbenzylamine, 3-trifluoromethylbenzylamine, 4-trifluoromethylbenzylamine, 8-fluoro-4-trifluoromethylbenzylamine, 2-fluoro-5-trifluoromethylbenzylamine, 2-chloro-3-trifluoromethylbenzylamine, 2-chloro-5-trifluoromethylbenzylamine, 4-chloro-3-trifluoromethylbenzylamine, 3,5-bis(trifluoromethyl)benzylamine, 2,4-bis(trifluoromethyl)benzylamine, 2,6-bis(trifluoromethyl)benzylamine and 2,5-bis(trifluoromethyl)benzylamine.

The following nonlimitative examples are illustrative of the present invention.

EXAMPLE 1

The first step of the process of the present invention was conducted as follows. At first, 8.79 g (50.5 mmol) of 4-trifluoromethylbenzaldehyde and 3.83 g (55.1 mmol) of hydroxylamine hydrochloride were dissolved in 12.5 ml of ethanol and 34 ml of water followed by the addition of 2.5 g of sodium hydroxide and stirring for 1 hour at room temperature. After adding ether and washing with dilute hydrochloric acid, the reaction liquid was further washed with saturated brine followed by drying with mirabilite and concentrating to obtain 9.25 g (48.2 mmol) of 4-trifluoromethylbenzaldehyde oxime (yield: 95.5%).

EXAMPLE 2

The second step of the process of the present invention was conducted as follows. At first, a 100 ml autoclave equipped with an electromagnetic stirrer was charged with 5.00 g (26 mmol) of 4-trifluoromethylbenzaldehyde oxime, 50 ml of 2M-ammoniacal methanol solution (containing 100 mmol of ammonia), and 0.25 g of a catalyst (i.e., a carbon powder (50% wet) carrying thereon 5% palladium), followed by introduction of hydrogen to have an inside pressure of 1 MPa. Then, the reaction mixture was stirred, while the reaction temperature was maintained at 20° C. and while hydrogen was gradually introduced into the autoclave in a manner to maintain the total pressure at 1 MPa. After conducting the reaction for 2 hr, the reaction was stopped, followed by removing the catalyst by filtration. As a result of analyzing the obtained reaction liquid by gas chromatography, 4-trifluoromethylbenzylamine was formed at a yield of 87.6%.

EXAMPLE 3

Example 2 was repeated except in that 50 ml of 2M-ammoniacal methanol solution were replaced with 50 ml of 2M-ammoniacal 2-propanol solution (containing 100 mmol of ammonia) and that the reaction was conducted for 3.5 hr in place of 2 hr. As a result of analyzing the obtained reaction liquid by gas chromatography, 4-trifluoromethylbenzylamine was formed at a yield of 95,0%.

EXAMPLE 4

The second step of the process of the present invention was conducted as follows. At first, a 1-liter autoclave equipped with a mechanical stirrer was charged with 300 g (1.59 mol) of 4-trifluoromethylbenzaldehyde oxime, 460 g of 2-propanol, and 15 g of a catalyst (i.e., a carbon powder (50% wet) carrying thereon 5% palladium), followed by introduction of 40 g of liquid ammonia and then introduction of hydrogen to have a pressure of 1 MPa. Then, the reaction mixture was stirred, while the reaction temperature was maintained at 20° C. and while hydrogen was gradually introduced into the autoclave in a manner to maintain the total pressure at 1 MPa. After conducting the reaction for 4 hr, the reaction was stopped, followed by removing the catalyst by filtration. As a result of analyzing the obtained reaction liquid by gas chromatography, 4-trifluoromethylbenzylamine was formed at a yield of 92.6%.

EXAMPLE 5

Example 4 was repeated except in that 460 g of 2-propanol were replaced with 460 g of toluene and that the reaction was conducted for 3 hr in place of 4 hr. As a result of analyzing the obtained reaction liquid by gas chromatography, 4-trifluoromethylbenzylamine was formed at a yield of 97.6%.

EXAMPLE 6

Example 4 was repeated except in that 460 g of 2-propanol were replaced with a combination of 368 g of 2-propanol and 92 g of toluene and that the reaction was conducted for 2 hr in place of 4 hr. As a result of analyzing the obtained reaction liquid by gas chromatography, 4-trifluoromethylbenzylamine was formed at a yield of 98.5%.

The entire disclosure of Japanese Patent Application No. 2000-112629 filed on Apr. 13, 2000, including specification, claims and summary, is incorporated herein by reference in its entirety.

What is claimed is:

1. A process for producing a trifluoromethylbenzylamine represented by the general formula (1), said process comprising reducing an oxime by hydrogen in an organic solvent in the presence of a catalyst and ammonia, said oxime being represented by the general formula (2),

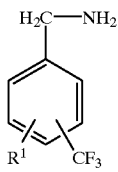

(1)

where $R^1$ represents hydrogen atom, a halogen atom selected from the group consisting of fluorine, chlorine, bromine and iodine, or trifluoromethyl group,

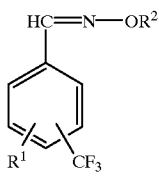

(2)

where $R^1$ is defined as above, and $R^2$ represents hydrogen atom, an alkyl group or an aralkyl group.

2. A process for producing a trifluoromethylbenzylamine represented by the general formula (1), said process comprising:
(a) reacting a trifluoromethylbenzaldehyde represented by the general formula (2) with a hydroxylamine represented by the general formula (3), thereby obtaining an oxime represented by the general formula (4); and
(b) reducing said oxime by hydrogen in an organic solvent in the presence of a catalyst and ammonia, thereby producing said trifluoromethylbenzylamine,

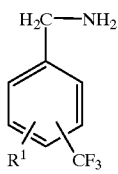

(1)

where $R^1$ represents hydrogen atom, a halogen atom selected from the group consisting of fluorine, chlorine, bromine and iodine, or trifluoromethyl group,

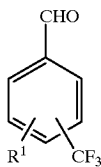

(2)

where $R^1$ is defined as above,

(3)

where $R^2$ represents hydrogen atom, an all group or an aralkyl group,

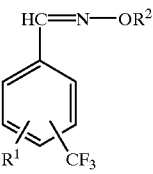

(4)

where $R^1$ and $R^2$ are defined as above.

3. A process according to claim 2, wherein said hydroxylamine is prepared by neutralizing an acid salt of said hydroxylamine with a base.

4. A process according to claim 3, wherein said base is selected from the group consisting of pyridine, triethylamine, N-methylmorpholine, sodium bicarbonate, sodium carbonate, potassium bicarbonate, potassium carbonate, calcium carbonate, lithium hydroxide, sodium hydroxide, and potassium hydroxide.

5. A process according to claim 3, wherein a molar ratio of said base to said acid salt of said hydroxylamine is at least 1.

6. A process according to claim 1, wherein said catalyst is a heterogeneous catalyst.

7. A process according to claim 6, wherein said heterogeneous catalyst is an activated carbon carrying thereon palladium.

8. A process according to claim 1, wherein said catalyst is in an amount of 0.0001 to 1 mol %, based on the number of moles of said oxime.

9. A process according to claim 1, wherein said reducing is conducted under a hydrogen pressure of 5 atmospheres or more.

10. A process according to claim 1, wherein said ammonia is in an amount of 1–10 moles per mol of said oxime.

11. A process for producing a trifluoromethylbenzylamine represented by the general formula (1), said process comprising:
(a) mixing together a trifluoromethylbenzaldehyde represented by the general formula (2), an acid salt of a hydroxylamine represented by the general formula (3), and a base, thereby obtaining an oxime represented by the general formula (4); and
(b) reducing said oxime by hydrogen in an organic solvent in the presence of an catalyst and ammonia, thereby producing said trifluoromethylbenzylamine,

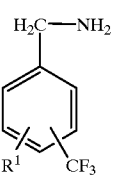

(1)

where $R^1$ represents hydrogen atom, a halogen atom selected from the group consisting of fluorine, chlorine, bromine and iodine, or trifluoromethyl group,

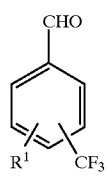
(2)
where R¹ is defined as above,
 (3)
where R² represents hydrogen atom, an akyl group or an aralkyl group,
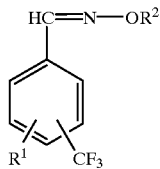
(4)
where R¹ and R² are defined as above.
* * * * *